US008445508B2

(12) United States Patent
Clemens (10) Patent No.: US 8,445,508 B2
(45) Date of Patent: May 21, 2013

(54) METHOD OF RESTORING THE INCRETIN EFFECT (75) Inventor: Anton H. Clemens, Madison, WI (US)

(73) Assignee: Neurendo Pharma, LLC, Madison, WI (US)

(*) Notice: Subject to any disclaimer, the term of this patent is extended or adjusted under 35 U.S.C. 154(b) by 207 days.

(21) Appl. No.: 12/906,735

(22) Filed: Oct. 18, 2010

(65) Prior Publication Data
US 2011/0034501 A1 Feb. 10, 2011

Related U.S. Application Data (62) Division of application No. 11/876,279, filed on Oct. 22, 2007, now Pat. No. 7,893,080.

(60) Provisional application No. 60/862,227, filed on Oct. 20, 2006.

(51) Int. Cl.
A61K 31/44 (2006.01)
A61K 31/215 (2006.01)
A61K 31/195 (2006.01)

(52) U.S. Cl.
USPC ........... 514/279; 514/529; 514/530; 514/563; 514/866

(58) Field of Classification Search
USPC .................... 514/279, 563, 529, 530, 866
See application file for complete search history.

(56) References Cited

U.S. PATENT DOCUMENTS

| | | | |
|---|---|---|---|
| 4,272,540 A | 6/1981 | Razdan et al. | |
| 4,451,470 A | 5/1984 | Ganti | |
| 4,478,840 A | 10/1984 | Smith, Jr. | |
| 4,619,936 A | 10/1986 | Balkanyi et al. | |
| 4,882,335 A | 11/1989 | Sinclair | |
| 5,086,058 A | 2/1992 | Sinclair et al. | |
| 5,208,250 A | 5/1993 | Cetenko et al. | |
| 5,428,066 A | 6/1995 | Larner et al. | |
| 5,457,208 A | 10/1995 | Portoghese et al. | |
| 5,665,383 A | 9/1997 | Grinstaff et al. | |
| 5,727,570 A | 3/1998 | Clemens | |
| 5,772,629 A | 6/1998 | Kaplan | |
| 5,866,595 A | 2/1999 | Pershadsingh et al. | |
| 5,878,750 A | 3/1999 | Clemens | |
| 5,891,909 A | 4/1999 | Soll et al. | |
| 5,925,657 A | 7/1999 | Seed et al. | |
| 6,026,817 A | 2/2000 | Clemens | |
| 6,087,385 A | 7/2000 | Pershadsingh et al. | |
| 6,242,196 B1 | 6/2001 | Spiegelman et al. | |
| 6,258,121 B1 | 7/2001 | Yang et al. | |
| 6,262,062 B1* | 7/2001 | Clemens | 514/282 |
| 6,268,357 B1 | 7/2001 | Orvig et al. | |
| 6,280,411 B1 | 8/2001 | Lennox | |
| 6,294,559 B1 | 9/2001 | Smith | |
| 6,309,660 B1 | 10/2001 | Hsu et al. | |
| 6,364,893 B1 | 4/2002 | Sahatjian et al. | |
| 6,369,039 B1 | 4/2002 | Palasis et al. | |
| 6,387,121 B1 | 5/2002 | Alt | |
| 6,409,716 B1 | 6/2002 | Sahatjian et al. | |
| 6,410,802 B1 | 6/2002 | Dasseux et al. | |
| 6,417,232 B1 | 7/2002 | Berge | |
| 6,419,692 B1 | 7/2002 | Yang et al. | |
| 6,441,025 B2 | 8/2002 | Li et al. | |
| 6,458,952 B1 | 10/2002 | South et al. | |
| 6,459,003 B1 | 10/2002 | Dasseux et al. | |
| 6,471,979 B2 | 10/2002 | New et al. | |
| 6,475,521 B1 | 11/2002 | Timmins et al. | |
| 6,500,824 B1 | 12/2002 | Portoghese et al. | |
| 6,528,520 B2* | 3/2003 | Clemens | 514/282 |
| 6,534,514 B1 | 3/2003 | Portoghese et al. | |
| 6,846,831 B2* | 1/2005 | Clemens | 514/282 |
| 6,919,310 B2* | 7/2005 | Clemens | 514/6.9 |
| 7,893,080 B2 | 2/2011 | Clemens | |
| 2005/0250701 A1 | 11/2005 | Clemens | |
| 2008/0108640 A1 | 5/2008 | Clemens | |

FOREIGN PATENT DOCUMENTS

| | | |
|---|---|---|
| BE | 8763852 | 11/1978 |
| EP | 0078434 | 5/1983 |
| EP | 0541192 | 5/1993 |
| GB | 2045758 | 11/1980 |
| WO | 9300337 | 1/1993 |
| WO | WO 9300337 A1 * | 1/1993 |
| WO | 9718781 | 5/1997 |
| WO | 9735608 | 10/1997 |
| WO | 9904795 | 2/1999 |
| WO | 9959997 | 11/1999 |
| WO | 0213759 | 2/2002 |
| WO | 0213801 | 2/2002 |
| WO | WO 0213759 A2 * | 2/2002 |
| WO | 02100390 | 12/2002 |
| WO | 03026635 | 4/2003 |
| WO | 2008051902 | 5/2008 |

OTHER PUBLICATIONS

McLaughlin, C.L. et al., "Influence of Nalmefene on Energy Balance and Glucose Regulation in Zucker Rats," Physiology & Behavior (1986) 37:899-908.

McLaughlin, C.L., el al., "Glucose, insulin, food intake and body weight responses of Zucker rates to nalmefene, an opiate antagonist," (1985) Abstract.

Windholz, M., et al., Editors, "The Merck Index an Encyclopedia of Chemicals, Drugs, and Biologicals," (1983) Tenth Edition, pp. 491-492.

(Continued)

Primary Examiner — Kevin E Weddington
(74) Attorney, Agent, or Firm — Whyte Hirschboeck Dudek S.C.; Michael J. Cronin (57) ABSTRACT The present invention relates to methods of treating metabolic syndrome, Type 2 diabetes mellitus, atherogenic dyslipidemia and/or obesity. The present invention also relates to methods of restoring the incretin effect, to restoring physiologic control of glucagon levels, to restoring first-phase insulin secretion, and to restoring the physiologic glucose-dependent insulin secretion. The methods of the present invention comprise administration of a selective κ-receptor antagonist, such as guanidinylated naltrindole (GNTI), or pharmaceutically acceptable derivatives thereof to a subject in need thereof.

5 Claims, 3 Drawing Sheets

OTHER PUBLICATIONS

Ofei, F., et al., "Effects of an Engineered Human Anti-TNF-α Antibody (DCP571) on Insulin Sensitivity and Glycemic Control in Patients with NIDDM," (1996) Diabetes 45:881-881.

Pan, Z.Z., "μ-Opposing action of the κ-opioid receptor," TiPS (1998) 19:94-94.

Paquot, N., "No Increased Insulin Sensitivity after a Single Intravenous Administration of Recombinant Human Tumor Necrosis Factor Receptor: Fc Fusion Protein in Obese Insulin-Resistant Patients," J Clin Endo Metab (2000) (3): 1316-1319.

Pearce, C., et al., "Effect of χ-oploid and AVP-V1 receptor antagonists on the compensatory hernodynarnic responses of anesthetized rats following acute hemorrhage," Can J Physiol Pharmacol (1992) 70 (Abstract).

Pfeiffer, A., et al., "Circulating Tumor Necrosis Factor α is Elevated in Male but Not Female Patients With Type II Diabetes Mellitus," Horm Metab Res (1997) 29:111-114.

Pfeifer, M.A., et al., "Insulin Secretion in Diabetes Mellitus," Amer J Med (1981) 70: 579-588.

Riepl R.L., et al., "Suppression of vagus-medaed panceatc poypepte elease by the μopae receptor agonis loperamide in man," Br J Clin Pharrnacol (1996)42:371-377.

Riepl, R.L., et al., "Pancreatic Polypeptide Release Induced by Ceruletide, Sham Feeding, and Hypoglycemia is Suppressed by Loperamide," Melab (1983) (Abstract).

Ruppin, H., "Review: loperamide—a potent antidiarrhoeal drug with actions along the alimentary tract," Aliment Pharmacol Ther (1987) 1(3):179-190.

Schultz. J.J., et al., "Mophine Mimics the Cadioprotective Effect of Ischemic Preconditioning via a Glibenclamde-Sensitive Mechanism in the Rat Heart," Circulation Research (1996) 78(6): 1100-1104.

Shaw, W.N. et al. "The effect of opioid antagonist LY255582 on body weight of the obese Zucke rat," Inter J Obesty (1991) 15:387-395.

Simpkins, J.W., et al., "Effects of the Narcotic Antagonist, Nalmefene, on Spontaneous and Insulin-Induced Food Intake and Body Weight Gain in Male Rats," (1985) (Abstract).

Sohel, M.S., et al., "Influence of Adrenergic Blockers and Aritilipemic Agents on Pharmacodynamic Actions of Morphine in Carbon Tetrachloride-Treated Rats," Toxicology and Applied Pharmacology (1974) 27:477-483.

Spanagel, R., et al., "Evidence that nor-binaltorphimine can function as an antagonist at multiple opioid receptor subtypes," Ep J Pharm (1994) 246:157-162.

Stephens, L.A., et al., "Tumor necrosis factor-alpha-activated cell death pathways in NIT-1 insulinoma cells and primary pancreatic beta cells," Endocrinology (1999) 140(7):3219-3217.

Stern, M.P., et al., "Lack of Awareness and Treatment of Hyperlipidemia in Type II Diabetes in a Community Survey," JAMA (1989) 262(3):360-364.

Swidan, S.Z., et al., "Effect of blood glucose concentrations on the developjent of chronic complications of diabetes mellitus," Pharmacotherapy (1998) 18(5): 961-972 (Abstract).

Szilagyi, J.E., "Physcosocial Stress Elevates Brood Pressure via an Opioid Dependent Mechanism in Normotensive Rats," Clin and Exper Hyper—Theory and Practice (1991) A13(8):1383-1394.

Table: "Characteristics of Sulfonylurea and Antihyperglycemic Drugs" Disorders of Carbohydrate Metabolism (1999) Chapter 13, p. 175.

Van Loon, G.R., et al., "β-Endorphin-Induced Stimulation of Central Sympathetic Outflow. β-Endorphin Increases Plasma Concentrations of Epinephrine, Norepinephrine, and Dopamine in Rats," Endocrinology (1981) 109(1):46-53.

Verspohl, E.J., et al., "The significance of μ-and detta-receptors in rat pancreatic islets for the opioid-mediated insulin release," Biochemica et Biophysica Acta (Netherlands) (1986) 888(2): 217-224 (Abstract).

Vink, R., et al., "K-Opioid antagonist improves cellular bioenergetics and recovery after traumatic brain injury," American Physiological Society (1991) R1527-R1532.

Wexler, B.C., "Naloxone Ameliorates the Pathophysiologic Changes Which Lead to and Attend an Acute Stroke in Stroke-Prone/SHR," Stroke (1984) 15(4): 630-634.

Wexler, B.C., et al., "Anti-opiate (Naloxone Suppression of Cushingoid Degenerative Changes in Obese/SHR," Inter J Obesity (1085) 9:77-91.

Yim, G.K., et al., "Opioids, feeding and anorexias," Federation Proceedings (1984) 43(14): 2893-2897 (Abstract).

Ahlgren, G., "Insulin-like action of morphine and certain morphine derivatives," Skand Arch Physiol (1930) 58:153-172.

Ahren, B., "Effects of β-Endorphin, met-Enkephalin, and Dynorphin A on Basal and Stimulated Insulin Secretion in the Mouse," Inter Jour Pancreatology (1898) 5:165-178.

Arias, A. et al., "Influence of Selective Agonist K Peripheral ICI-204448 (ICI) on Blood Pressure of Rats Pretreated with Clonidine (CLO)," Abstract (1997).

Arioglu, E., et al., "Efficacy and Safety of Troglitazone in the Treatment of Lipodystrophy Syndromes," Ann Int Med (2000) 133(4): 263-274.

Atkinson, R.L., et al., "Effects of long-term therapy with naltrexone on body weight in obesity," Clin Pharmacol Ther (1985) 38(4): 419-422.

Awoke, S., et al.. "Alterations of plasma opioid activity in human diabetics," Life Sciences (1984) 34:1999-2006.

Bailey, C.J., et al., "Increased responsiveness to glucoregulatory effect of opiates in obese-diabetic ob/ob mice," (Abstract) Diabetologia (1987) 30(1):33-37.

Bernardi, P., et al., "Endogenous opioid system in acute myocardial infarction," Abstract (1954).

Caldwell, R.W., et al., "Actions of the Opioid Antagonist, Nalmefene, and Congeners on Reperfusion Cardiac Arrhythmias and Regional Left Coronary Blood Flow," Pharmacology 41:161-166 (1990).

Carr, K.D., et al., "The role of opioids in feeding and reward elicited by lateral hypothalamic electrical stimulation," Life Sciences (1983) 33(1):563-566.

Chance, W.T., et al., "Analysis of the interaction of naltrexone with eating following adrenergic and cholinergic stimulation of the hypothalamus," Neuropharmacology (1982) 21:929-932.

Cole, J.L., et al., "Evaluation of Chronic Opioid Receptor Antagonist Effects Upon Weight and intake Measurers in Lean and Obese Zucker Rats," Peptides (1997) 18(8):1201-1207.

Drolet, G., et al., "Endogenous opioids tonically inhibit the depressor neurons in the caudal ventrolateral medulla of rabbits: Mediation through δ and κ-receptors," Neuropharmacology (1991) 30(4):383-390.

Felber, J.P., et al., "Effect of a 3-Day Fast on Glucose Storage and Oxidation in Obese Hyperinsulinemic Diabetics," Metablolism (1981) 30(2)184-189.

Felber, J.P., et al., "Glucose Storage and Oxication in Different Degrees of Human Obesity Measured by Continuous Indirect Calorimetry," Diabetologia (1981) 20:39-44.

Ferlito, S., "Influenza dei peptide oppioidi sul metabolism glucidico," II Progresso Medico, Roma (1985) 41:639-655.

Foss, M.C., et al., "Restoration of Glucose Homeostasis in Insulindependent Diabetic Subjects, An Inducible Process," Diabetes (1982) 31:46-53.

Garris, D.R., "Nalmefene, an opiate antagonist, effectively modulates insulin receptor binding in the peripheral tissues of C57BL/KsJ mice," Med Sci Res (1988) 16:301-302.

Gautret, B., et al., "Vagally mediated reflex and cardiac slowing induced by loperamide in rats," Ep J Pharm (1985) 107:157-160.

Giugliano, D., et al., "β-Endorphin and islet hormone release in type-2 diabetes mellitus. The effects of normoglycemia, enkephalin, naloxone and somatostatin," Diabete et Metabolisme (1987) 13(6):618-624 (Abstract).

Giugliano, D., et al., "Impaired insulin secretin in human diabetes mellitus. The effect of naloxone-induced opiate receptor blockade," Diabetes (1982) 31(4):367-370 (Abstract).

Giugliano, D., et al., "Sensitivity to β-Endorphin as a Cause of Human Obesity," Metabolism (1987) 36(10): 974-978.

Givens, J.R., et al., "Reduction of Hyperinsulinemia and Insulin Resistance by Opiate Receptor Blockade in the Polycystic Ovary Syndrome with Acanthosis Nigricans," J Clin Endocrinology and Metabolism (1987) 64(2): 377-382.

Got, I., et al., "Les Particularities du Traitement Medical chez les Arteritiques Diabetiques," J Maladies Vascularies (Paris) (1993) 18:30-36.

Green, I.C., et al., "Effect of enkephalins and morphine on insulin secretion from isolated rat islets," Diabetologia (Germany) (1980) 19(2): 158-161 (Abstract).

Green, I.C., et al., "Effect of enkephalins and morphine or insulin secretion from isolated rat islets," Diabetologia (Germany) (1980) 19(2): 158-161 (Abstract).

Green, I.C., et al., "Opiate-prostaglindin interactions in the regulation of insulin secretion from rats islets on Langerhans in vitro," Life Sciences (1988) 42(21):2123-2130.

Gupta, B., et al., "Glucose Homeostasis and Drugs Acting on CNS: Interaction with Antidiabetic Agents," Indian J Pharm (1994) 26: 169-178.

Hansen, B.C., et al., "Diabetes and the Metabolic Syndrome in Monkeys: Use as Reserch Mdels,".

Herz, A., "Bidirectional effects of opioids in motivational process and the involvement of D1 dopamine receptors," NIDA Res Monogr (1988) 90: 17-26 (Abstract).

Hotamisligil, G., et al., "Tumor necrosis factor α inhibits signaling from the insulin receptor," Proc Natl Acad sci (1994) 91: 4854-4854.

Hotamisligil, G., et al., °Adipose Expression of Tumor Necrosis Factor-α: Direct Role in Obesity-Linked Insulin Resistance, Science (1993) 259:87-91.

Imai, N., et al., "Effects of opioid antagonism in congestive heart failure," (1985) (Abstract).

Jacob, C., "Studies on the role of tumor necrosis factor in murine and human autoimmunity," J Autoimmun (1992) 5 (Supp A): 133-143.

Khawaja, Z., et al., "Increased Sensitivity to Insulin-Releasing and Glucoregulatory Effects of Dynorphin A1-13 and U 50488h in ob/ob Versus Lean Mice," Diabetes (1990) 39:1289-1297.

Kurtz, B.R., et al., "Nalmefene, an orally active opiate antagonist, reduces insulin resistance and caloric intake in obese women with polycystic ovaries and acanthosis nigricans," (1985) (Abstract).

Landgraf, R., et al., "Prolactin: A Diabetogenic Hormone," Diabetologia (1977) 13:99-104.

Leslie, R.D., et al., "Sensitivity to Enkephalin as a Cause of Non-Insulin Dependent Diabetes," The Lancet Feb. 17, 1979 pp. 341-343.

Levine, A.S., et al., "Nor-binaltorphimine decreases deprivation and opioid-induced feeding," Brain Research (1990) 534: 60-64 (Abstract).

Levine, A.S., et al., "Effect of chronic administration of morphine and nalmefene on food intake and body weight in diabetic and control rats," (1985) (Abstract).

Liang, B.T., et al., "Direct Preconditioning of Cardiac Myocytes via Opioid Receptors and KATP Channels," Circ Res (1999) 84:1396-1400.

Liu, I.M., et al., "Activation of opioid μ-receptor by loperamide to lower plasma glucose in streptozolocin-induced diabetic rats," Neuroscience Letters (1999) 265:183-186.

Marsboom, R., et al., "Lopeamde (R 18 553), a Novel Type of Antidiarheal Agent" Drug Res (1974) 24:10 1645-1649.

Martinez, E., et al., "Metabolic abnormalities and body fat redistribution in HIV-1 infected patients: the lipodystrophy syndrome," Curr Opin Infect Dis (1999) 12:13-19.

McCormack, K.J., et al., "Opioid Receptors and Myocardial Protection Do Opioid Agonists Possess Cardioprotective Effects?" Clin Drug Invest (1998) 15(5): 445-454.

McCubbin, J.A., et al., "Opioidergic Inhibition of Circulatory and Endocrine Stress Responses in Cynomolgus Monkeys: A Preliminary Study," Psychosomatic Medicine (1993) 55: 23-28.

McInotsh, M.A., et al., "The effects of opioid receptor selective antagonists and agonists following coronary artery occlusion in anaesthetized rats," (1990) (Abstract).

McIntosh, M., et al., "Effects of selective opioid receptor agonists and antagonists during myocardial ischaemia," Ep J of Pharmacology (1992) 210: 37-44.

McLaughlin, C.L., et al., "Nalmefene Decreases Meal Size, Food and Water Intake and Weight Gain in Zucker Rats," Pharmacology, Biochemistry & Behavior (1983) 19:235-240.

Buzi, F. et al., "Loperamide test: a simple and highly specific screening test for hypercortisolism in children and adolescents," Acta Paediatr. (1997) 86(11):1177-1180.

Caldara, R. et al., "Effect of loperamide, a peripheral opiate agonist, on circulating glucose, free fatty acids, insulin, C-peptide and pituitary hormones in healthy man," Eur. J. Clin. Pharmacol. (1981) 21(3):185-188.

Carroll, Ivy, et al. "Pharmacological properties of JDTic: a novel k-opioid receptor antagonist", European Journal of Pharmacology 501, 111-119 2004.

Drucker, D.J., "Enhancing incretin action for the treatment of type 2 diabetes," Diabetes Care (2003) 26:2929-2940.

Edelman, S.V., "Prescribing oral antidiabetic agents: general considerations," Clinical Diab. (1998) 16(1):37-40.

EP Supplemental Search Report for EP07844505.3 mailed Mar. 15, 2010.

Evans, A.J. et al., "Recent developments and emerging therapies for type 2 diabetes mellitus," Drugs R&D (1999) 2 (2):75-94.

Greenbaum, C.J. et al., Impaired beta-cell function, incretin effect, and glucagon suppression in patients with type 1 diabetes who have normal fasting glucose, Diabetes (2002) 51:951-957.

Grundy, S.M. et al., "Definition of metabolic syndrome: report of the National Heart, Hung, and Blood Institute/American Heart Association Conference on scientific issues related to defmition," Circulation (2004) 109:433-438.

Grundy, S.M. et al., "Diagnosis and management of the metabolic syndrome: an American Heart Association/National Heart, Lung, and Blood Institute scientific statement: executive summary," Circulation (2005) 112:e285-e290.

Grundy, S.M. et al., "Diagnosis and management of the metabolic syndrome: an American Heart Association/National Heart, Lung, and Blood Institute scientific statement: executive summary," Circulation (2005) 112:2735-2752.

Herz, A., "Opioid reward mechanisms: a key role in drug abuse?," Can. J. Physiol. Pharmacol. (1998) 76(3):252-258.

Herz, A., "Problems of drug dependence 1988," Proceedings of the 50th Annual Scientific Meeting, The Committee on Problems of Drug Dependence, Inc., NIDA Res. Monogr. (1988) 90:17-26.

Hiriart, M. et al., "Muscarinic modulation of insulin secretion by single pancreatic beta-cells," Mol. Cell Endocrinol. (1993) 93(1):63-69.

Holst, J.J. et al., "The incretin approach for diabetes treatment. Modulation of islet hormone release by GLP-1 agonism," Diabetes (2004) 53(3):S197-S204.

Jarosz, P.A., et al. "Effect of chronic kappa opioid receptor antagonism on body weight and food intake in obese Zucker rats." vol. 26, No. 1-2, 2000 Abstract.

Jewett, D.C. et al., "The kappa-opioid antagonist GNTI reduces U50,488-, DAMGO-, and deprivation-induced feeding, but not butorphanol- and neuropeptide Y-induced feeding in rats," Brain Res. (2001) 909(1-2):75-80.

Jivegard, L. et al., "The influence of morphine, looperamide and naloxone on gallbladder response to prostaglandin E2 in the anaesthetized cat," Acta Physiol. Scand. (1986) 127:275-279.

Jones, R.M. et al., "Mutational evidence for a common lc antagonist binding pocket in the wild-type K and mutant KK308E1 opioid receptors," J. Med. Chem. (1998) 41(25):4911-4914.

Kindmark, H. et al., "Glucose-dependent insulinotropic hormone potentiates the hypoglycemic effect of glibenclamide in healthy volunteers: evidence for an effect on insulin extraction," J. Clin. Endocrinol. Metab. (2001) 86 (5):2015-2019.

Lewis, J.T. et al., "Glucose-dependent insulinotropic polypeptide confers early phase insulin release to oral glucose in rats: demonstration by a receptor antagonist," Endocrinology (2000) 141(10):3710-3716.

Lewis, J.W., "Buprenorphine," Drug & Alcohol Dependence (1985) 14:363-372.

Malaisse, W.J. et al., "insulinotropic action of beta-L-glucose pentaacetate," Am. J. Phys. (1998) 276(6/1):E993E1006.

McQuay, H.J. et al., "Clinical effects of buprenorphine during and after operation," Br. J. Anaesth. (1980) 52:1013-1019.

Meier, J.J. et al., "Postprandial suppression of glucagon secretion depends on intact pulsatile insulin secretion. Further evidence for the intraislet insulin hypothesis," Diabetes (2006) 55:1051-1056.

Merz, H. et al., "Structural features of opioid kappa agonists and antagonists," Adv. Biochem. Psychopharm. (1974) 8:91-107.

Metcalf, M.D. et al., "Kappa opioid antagonists: past successes and future prospects," AAPS Journal (2005) 7(3): E704-E722.

Nauck, M.A. et al., "Gastric inhibitory polypeptide and glucagon-like peptide-1 in the pathogenesis of type 2 diabetes," Diabetes (2004) 53(Suppl. 3):5190-S196.

Niwa, T. et al., "Acetylcholine activates intracellular movement of insulin granules in pancreatic beta-cells via inositol triphosphate-dependent mobilization of intracellular Ca2+," Diabetes (1998) 47:1699-1706.

Pan, Z.Z., "ti-opposing actions of the ic-opioid receptor," Trends Pharmacol. Sci. (1998) 19(3):94-98.

Parkes, D.G. et al., "Insulinotropic actions of exendin-4 and glucagon-like peptide-1 in vivo and in vitro," Metabolism (2001) 50(5):583-589.

Portoghese, P.J. et al., "TENA, a selective kappa opioid receptor antagonist," Life Sci. (1984) 36:801-805.

Portoghese, P.J. et al., "Binal torphimine and non-binaltorphimine, potent and selective kappa-opioid receptor antagonists," Life Sci. (1987) 40:1287-1292.

Raskin, P. et al., "Repaglinide/troglitazone combination therapy. Improved glycemic control in type 2 diabetes," Diabetes Care (2000) 23(7):979-983.

Stevens, W.C. et al., "Potent and selective indolomorphinan antagonists of the kappa-opioid receptor," Med. Chem. (2000) 43(14):2759-2769.

Szkudelski, T. et al. "The effect of myo-inositol on ethanol-induced metabolic changes and insulin concentration in the rat," Arch Physiol. Biochem. (1999) 107(4):334-337.

International Search Report and Written Opinion for Application No. PCT/US07/82084 dated Mar. 6, 2008 (7 pages).

\* cited by examiner

METHOD OF RESTORING THE INCRETIN EFFECT

CROSS-REFERENCE TO RELATED APPLICATIONS

This application is a divisional application of application Ser. No. 11/876,279 filed Oct. 22, 2007, which is a non-provisional application of U.S. Provisional Application No. 60/862,227, filed Oct. 22, 2006. The Ser. No. 11/876,279 application claims priority to U.S. Provisional Application No. 60/862,227 filed Oct. 22, 2006 all of which are incorporated by reference in their entireties herein.

STATEMENT REGARDING FEDERALLY SPONSORED RESEARCH

Not applicable.

INTRODUCTION

Insulin secretion is stimulated to greater extent by oral intake of glucose than by intravenous intake of glucose. This effect, which is called the incretin effect, is estimated to be responsible for more than half of the insulin response to glucose. The incretin effect is caused mainly by the two intestinal insulin-stimulating hormones, glucagon-like peptide-1 (GLP-1) and glucose-dependent insulinotropic polypeptide (GIP). In patients with Type 2 diabetes mellitus, and other components of the metabolic syndrome, such as impaired glucose tolerance, atherogenic dyslipidemia, overweight and obesity, the incretin effect is either greatly impaired or absent.

The rapid and sizable increase in insulin release initiated by the incretin effect begins within two minutes of nutrient ingestion and continues for up to 15 minutes. This post-meal increase in insulin is referred to as first phase insulin secretion. A second phase of insulin secretion follows and is sustained until normal blood glucose levels are restored. Clinical observations reveal that patients with metabolic syndrome disorders such as Type 2 diabetes mellitus, impaired glucose tolerance, and obesity are characterized by progressive reductions in the magnitude of first-phase insulin secretion, insulin resistance, and beta-cell dysfunction, creating a new pathogenic platform shared by all components of the metabolic syndrome. Beta-cell dysfunction is, in turn, characterized by its two contributing components: (1) the progressive impairment of insulin production, and (2) the progressive impairment of physiologic control of insulin release. It follows, that the metabolic disorders should be correctable by the treatment, or restoration, of the failing components of the underlying pathogenic platform of insulin resistance and beta-cell dysfunction.

Glucose intolerance includes a continuous range of impairments in carbohydrate metabolism. Type 2 diabetes mellitus, impaired glucose tolerance, and impaired fasting glucose, among other conditions associated with glucose intolerance, have been implicated as risk factors contributing to heart disease, stroke, overweight, obesity, hypertension, and atherogentic dyslipidemia.

The pathogenesis of obesity is associated with other components of the metabolic syndrome, like atherogenic dyslipidemia, and glucose intolerance, the magnitude of which may progress over time. Threshold levels for pharmacological treatment have, therefore, been revised downward on several occasions in order to intervene at an earlier stage in the epidemic expansion of the affected population, and the corresponding health care expenditures. Non-insulin therapies are available to reduce endogenous gluconeogenesis or improve peripheral insulin sensitivity, e.g., metformin, sulfonylureas or thiazolidinediones (TZD). However, these therapies fail to restore first-phase insulin release or the incretin effect. Importantly, enhanced early insulin release is associated with improved overall glucose tolerance. There is, currently, no treatment available to restore or reactivate the natural physiology of the native incretin system.

SUMMARY

The present invention relates to methods of treating metabolic syndrome, Type 2 diabetes mellitus, atherogenic dyslipidemia and/or obesity. The present invention also relates to methods of restoring the incretin effect, to restoring physiologic control of glucagon levels, to restoring first-phase insulin secretion, and to restoring the physiologic glucose-dependent insulin secretion.

The methods of the present invention comprise administration of a selective κ-receptor antagonist such as guanidinylated naltrindole (GNTI), or a pharmaceutically acceptable derivative thereof, to a subject in need thereof. The selective κ-receptor antagonist may be administered daily, weekly or at any suitable time interval. Administration may be sublingually, orally, enterally, parenterally, topically or systemically. The selective κ-receptor antagonist may be co-administered with an insulinotropic agent. The insulinotropic agent may be an extended release formulation.

DETAILED DESCRIPTION

It has surprisingly been discovered that the administration of a selective κ-receptor antagonist, such as GNTI, is useful in the treatment of metabolic syndrome by targeting the incretin effect. The term "selective κ-receptor antagonist" means a κ-receptor antagonist characterized by its μ/κ antagonism $K_e$ selectivity ratio, as defined in *J. Med. Chem* 43, 2759-2769 (2000), the ratio required for this method being >35. Suitably, the selective κ-receptor antagonist acts peripherally. That is, it is substantially free of CNS activity.

The term "metabolic syndrome" may include, but is not limited to, atherogenic dyslipidemia, pre-diabetes, overweight/obesity, Type 2 diabetes mellitus and essential hypertension. The pathogenesis of obesity is associated with other components of the metabolic syndrome, e.g., atherogenic dyslipidemia, and glucose intolerance, the magnitude of which may progress, from its initial stages characterized by impaired fasting glucose, followed by impaired glucose tolerance and culminating in Type 2 diabetes mellitus. Administration of a selective κ-receptor antagonist, or a pharmaceutically acceptable derivative thereof has been found to restore the incretin effect, restore physiological control of glucagon levels in response to ingested nutrition, restore first-phase insulin secretion, restore glucose-dependent insulin secretion, reduce weight gain and/or lower weight in a subject without co-administration of a μ-agonist.

As will be appreciated, the methods described herein may be useful in both research and clinical settings, suitably wherein treatment of certain disease states are implicated, including, but not limited to, impaired glucose tolerance, Type 2 diabetes mellitus, diminished or absent first-phase insulin secretion, and obesity.

The administration of a selective κ-receptor antagonist to a subject in need thereof may treat metabolic syndrome. Administration of a selective κ-receptor antagonist may treat metabolic syndrome by restoring the incretin effect, by restoring physiologic control of glucagon levels, by restoring the physiologic glucose dependent insulin secretion, and/or by restoring first-phase insulin secretion. Suitably, the administration of a selective κ-receptor antagonist may also treat overweight, atherogenic dyslipidemia obesity or Type 2 diabetes mellitus by restoring the incretin effect, by restoring physiologic control of glucagon levels, by restoring the physiologic glucose dependent insulin secretion, and/or by restoring first-phase insulin secretion.

The administration of a selective κ-receptor antagonist to a subject in need thereof restores the incretin effect. In a subject having a normal response to oral nutrient administration, the release of the insulinotropic hormones, GIP and GLP-1, results in an increase in insulin secretion. This is called the "incretin effect". As used herein, to "restore," for example, with respect to the incretin effect, suitably includes enhancing, potentiating, increasing, reestablishing, re-activating, or improving the physiological state. For example, a subject having Type 2 diabetes mellitus may exhibit diminished or even zero incretin effect, i.e., diminished or no activity of GIP or GLP-1, or diminished or no increase in insulin secretion upon nutrient administration. Consequently, to "restore" the incretin effect suitably increases, though does not necessarily normalize, GIP or GLP-1 activity or insulin secretion upon nutrient administration in a subject. The subject is suitably a mammal, such as a human, dog, cat, primate, etc.

The administration of a selective x-receptor antagonist may restore physiologic control of glucagon levels in a subject in need thereof. As used herein, to "restore," for example with respect to physiologic control of glucagon levels, suitably includes, decreasing, lowering, regulating, reestablishing, or improving the physiologic state. In a subject having a 'normal' physiologic response to nutrient administration, physiologic control of glucagon primarily responds to blood glucose levels, i.e., as blood glucose levels decline, glucagon is released from the α cells of the islets of Langerhans in the pancreas, and act on the liver to induce gluconeogenesis, i.e., endogenous glucose production, and/or glycogenolysis. Conversely, glucagon release decreases in response to increasing blood glucose levels. Additionally, glucagon levels decrease in response to release of insulin by pancreatic β-cells. Consequently, in a subject having abnormal insulin production or release in response to increasing blood glucose levels, glucagon release may remain abnormally high and result in hyperglucagonemia which further exacerbates conditions such as Type 2 diabetes mellitus and impaired glucose tolerance.

Normal insulin secretion from the pancreatic β cells is biphasic. The initial release of insulin that acts on the pancreatic α cells to decrease glucagon is referred to as the first-phase of insulin secretion. First-phase insulin secretion is characterized by a rapid and sizable increase in insulin, beginning within two minutes of nutrient ingestion, and continuing for 10-15 minutes. For example, in Examples 3 and 4, first-phase insulin secretion can be seen at the 5-minute time point coupled with a corresponding drop in glucagon levels. Two minutes later, blood glucose levels show an initial decrease. The second phase of insulin secretion follows and insulin secretion peaks approximately 1-2 hours following nutrient ingestion. Insulin secretion continues until normal blood glucose levels are restored. Often, in subjects having impaired glucose tolerance, first-phase insulin secretion is reduced and it is believed that the reduction in first-phase insulin secretion may be a preliminary sign in the progression of Type 2 diabetes mellitus.

The administration of a selective κ-receptor antagonist restores first-phase insulin secretion in a subject in need thereof. The administration of a selective κ-receptor antagonist may restore the physiologic glucose dependent insulin secretion in a subject in need thereof, and a selective κ-receptor antagonist may restore the physiologic control of glucagon release.

The methods described herein restore the incretin effect, first-phase insulin secretion and/or physiologic insulin secretion through administration a selective κ-receptor antagonist. Suitably, the present invention may also provide a method of treating Type 2 diabetes mellitus, atherogenic dyslipidemia, obesity/overweight or metabolic syndrome through administration of a selective κ-receptor antagonist. The administration of an effective amount of a selective κ-receptor antagonist may reduce weight gain or lower weight in a subject in need thereof.

Suitably, an insulinogenic agent may be used in combination with a selective κ-receptor antagonist. An "insulinogenic agent" stimulates, participates in the stimulation of, or potentiates the biosynthesis of insulin by the pancreatic β-cells. Examples of insulinogenic agents include sulfonylureas, repaglinide, nateglinide, mitiginide and BTS-67-582. Suitably, the insulinogenic agent is provided in an extended release composition, i.e., the insulinogenic agent is formulated such that it is released over a period of time. An extended release insulinogenic agent acts to potentiate the synthesis of insulin.

Pharmacologically equivalent derivatives of a selective κ-receptor antagonist include any pharmaceutically acceptable salts, hydrates, esters, ethers, amides, or any other derivative which is not biologically or otherwise undesirable and induces the desired pharmacological and/or physiological effect.

The selective κ-receptor antagonist and the insulinogenic agent (together referred to as "active agent") are suitably administered in a pharmaceutical composition, which include the active agent(s) and one or more pharmaceutically acceptable excipients such as stabilizers, anti-oxidants, binders, coloring agents, emulsifiers. The pharmaceutical composition may be administered as a solution, an emulsion, a suspension, a dispersion, a transdermal patch, a pill, a tablet or a capsule. One of ordinary skill in the art would be able to formulate the pharmaceutical composition using the appropriate solid, liquid or gel carriers. The selective κ-receptor antagonist and the insulinogenic agent may be formulated separately or together.

Various methods for administration of the active agent(s) may be employed. For example, the active agent(s) may be given sublingually, orally, enterally, parenterally, topically, systemically or may be injected intravascularly, subcutaneously, peritoneally, and so forth. The active agent(s) may be administered weekly, semi-weekly, daily, or multiple times a day, such as twice a day or three times a day. The selective κ-receptor antagonist and the insulinogenic agent may be administered concurrently. Alternatively, the selective κ-receptor antagonist may be administered before or after administration of the insulinogenic agent.

The dosage of a selective κ-receptor antagonist will vary widely, depending upon the frequency of administration, the manner of administration, and the clearance of a selective κ-receptor antagonist from the subject. It will be appreciated that the specific dosage administered in any given case will be adjusted in accordance with the condition of the subject and other relevant medical factors that may modify the activity of the selective κ-receptor antagonist. For example, the specific dose for a particular patient depends on age, body weight, general state of health, diet, the timing and mode of administration, the rate of excretion and medicaments used in combination. For example, a suitable weekly dose of a selective κ-receptor antagonist may be less than about 300 ng per kg of body weight. Alternatively the weekly dose of a selective κ-receptor antagonist may be less than about 200 ng per kg of body weight, less than about 150 ng per kg of body weight or less than about 100 ng per kg of body weight. The initial dose may be larger, followed by smaller maintenance doses. The dose may be administered as infrequently as weekly or biweekly, or fractionated into smaller doses and administered daily, semi-weekly, etc. to maintain an effective dosage level. A suitable daily dosage of a selective κ-receptor antagonist is less than about 80 ng per kg of body weight. Alternatively the daily dosage of a selective κ-receptor antagonist may be less than about 50 ng per kg of body weight, less than about 25 ng per kg of body weight, or less than about 20 ng per kg of body weight.

The dosage of the insulinogenic agent will vary depending on the condition of the subject or other relevant medical factors that modify the activity of the insulinogenic agent or the response of the subject. For example, the specific dose for a particular patient depends on the severity of glucose intolerance, age, body weight, general state of health, diet, the timing and mode of administration, the rate of excretion, and medicaments used in combination. The initial dose may be larger, followed by smaller maintenance doses. The dose may be formulated for extended release, and administered as infrequently as weekly or biweekly, or fractionated into smaller doses and administered daily, semi-weekly, weekly, etc. to maintain an effective dosage level. One of ordinary skill in the art would be able to determine the appropriate dose of the insulinogenic agent.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent application's are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical range recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. For further example, if a dosage is stated as less than about 250 ng/kg of body weight, it is intended that values such as 50 to 200 ng per kg of body weight, and 100 to 200 ng per kg of body weight are expressly enumerated in this specification. These are only examples of what is specifically intended.

The present invention is further explained by the following examples, which should not be construed by way of limiting the scope of the present invention.

EXAMPLE 1

Evaluation of Blood Glucose in a Human

The daily blood glucose profile of a male subject with early stage, [non-insulin dependent] Type 2 diabetes was monitored during extended periods of administration of guanidinylated naltrindole (GNTI). A summary of the blood glucose reading is shown in Table 1.

TABLE 1

| Summary | |
|---|---|
| Average, mg/dL | 92 |
| Highest Blood Glucose, mg/dL | 127 |
| Lowest Blood Glucose, mg/dL | 61 |
| Standard Deviation, mg/dL | 14 |
| Number of Glucose Readings | 227 |
| Days Covered | 15 |
| Number of Days Without Tests | 0 |
| Average Readings Per Day | 15.1 |
| Deleted Glucose Readings | 0 |
| Control Readings | 13 |
| Deleted Control Readings | 0 |
| Average of Recorded Daily Insulin Shots | |
| with All Days Covered: | 0.0 |
| with Days with Insulin Records: | 0.0 |

A weekly dose of about 70 ng/kg was administered. The subject's blood glucose (BG) levels were measured in mg/dL at time intervals as shown in Table 2.

TABLE 2

| | Overall | Early AM | Morning | Midday | Evening | Night |
|---|---|---|---|---|---|---|
| Time Range | | 0.0:00 04:59 | 05:00 10:59 | 11:00 14:59 | 15:00 18:59 | 19:00 23:59 |
| Average, mg/dL | 92 | 79 | 90 | 92 | 91 | 95 |
| Std. Dev. mg/dL | 14 | 3 | 12 | 14 | 13 | 15 |
| Number of Readings | 227 | 4 | 65 | 56 | 44 | 58 |
| Very Highs, >300 | | | | | | |
| Highs, 156-300 | | | | | | |
| In Target, 65-155 | 98% | 100% | 97% | 98% | 100% | 97% |
| Lows, 51-64 | 2% | | 3% | 2% | | 3% |
| Very Lows, <51 | | | | | | |

Figure 1:
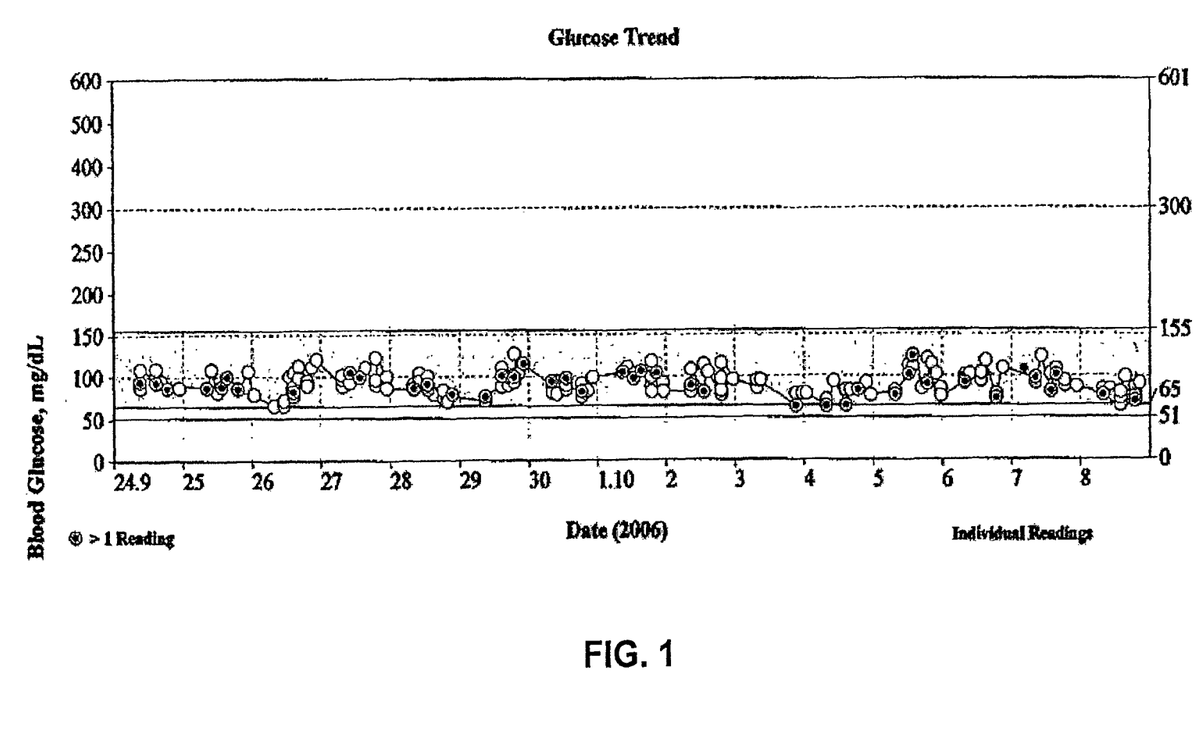
FIG. 1 illustrates the blood glucose readings of a male subject treated with GNTI over an extended period of time as described in Example 1.
Figure 2:
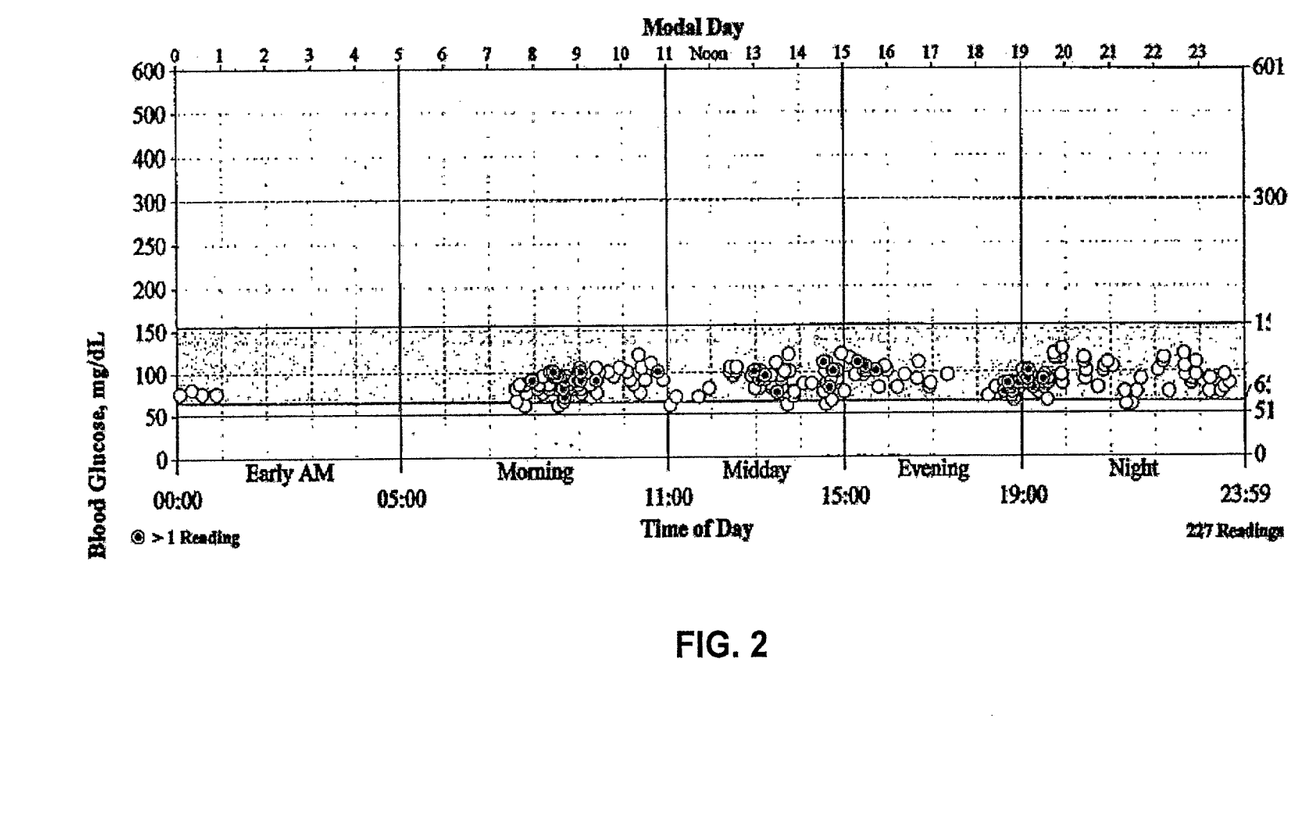
FIG. 2 illustrates the blood glucose readings of a male subject treated with GNTI over a modal week as described in Example 1.
Figure 3:
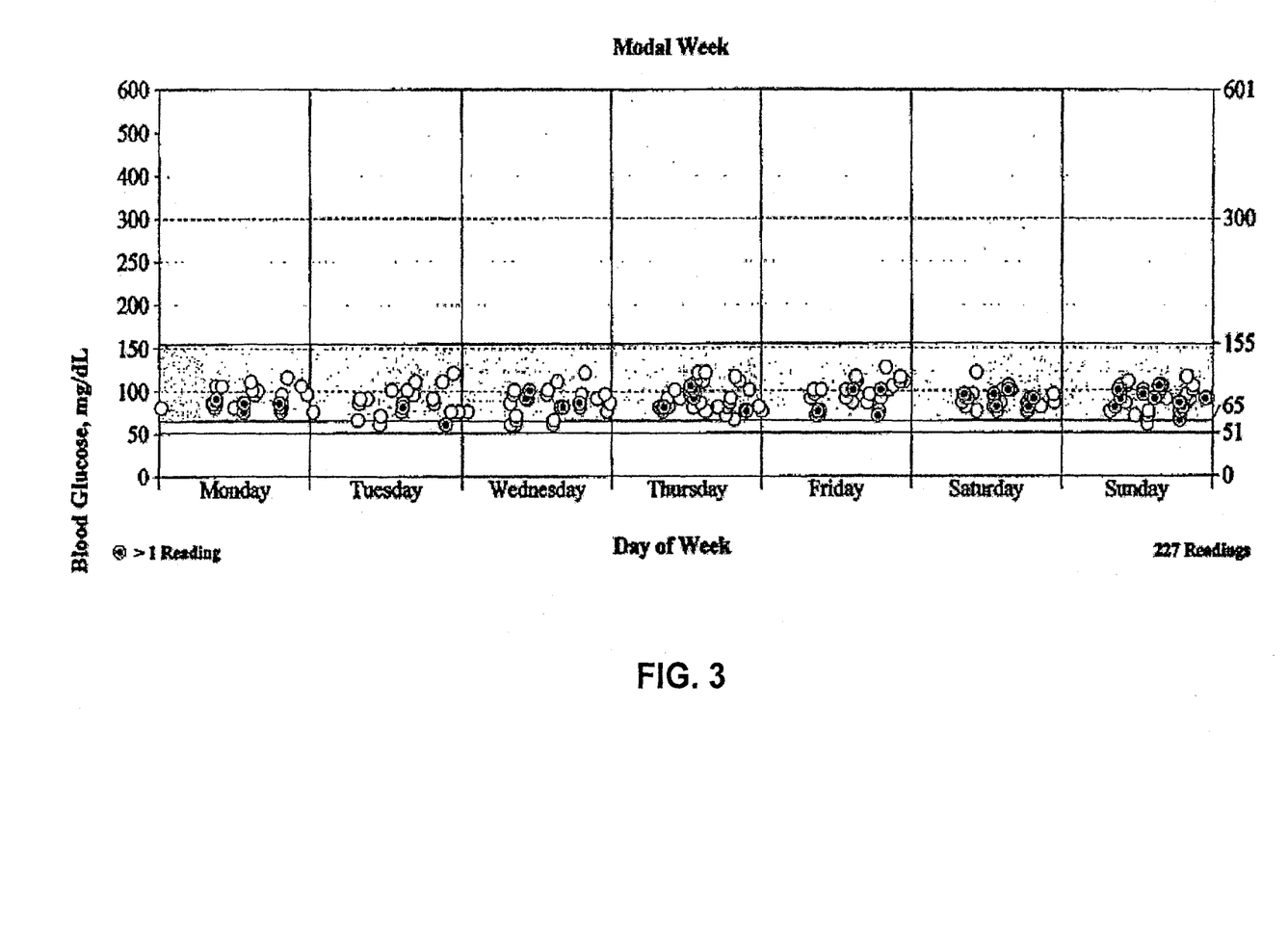
FIG. 3 illustrates the blood glucose readings of a male subject treated with GNTI over a modal day as described in Example 1.

FIGS. 1-3 illustrate the blood glucose readings over an extended period of time, a modal week and a modal day. The target blood glucose range was 65-155 mg/dL. Table 3 illustrates that 98% of the readings were within the target range. The other 2% of the readings fell below the target range and fell between 51-64 mg/dL. Note that none of these readings were in the hypoglycemic range.

TABLE 3

| Reading/Range | | |
| --- | --- | --- |
| Glucose Ranges, mg/dL | Number | Percent |
| Very High (301-601) | 0 | 0% |
| High (156-300) | 0 | 0% |
| Target (65-155) | 222 | 98% |
| Low (51-64) | 5 | 2% |
| Very Low (0-50) | 0 | 0% |

FIGS. 1-3 illustrate the subject's blood glucose readings over an extended period of time, a modal week, and a modal day. Accordingly, 227 blood glucose readings were taken, averaging 92 mg/dL over a 15 day period. 98% of all readings were between 65 and 127 mg/dL, and 2% between 61 and 65, representing a very narrow overall spread. These data exemplify glucose dependent insulin secretion, one of the characteristics of GNTI mediated incretin targeted treatment of Type 2 diabetes mellitus subjects.

Table 4 illustrates the blood glucose statistics by day of week. These data illustrate that once weekly administration of GNTI aided in maintaining blood glucose levels within the target range.

TABLE 4

| Blood Glucose Statistics by Day of Week, mg/dL | | | | | | | | | |
| --- | --- | --- | --- | --- | --- | --- | --- | --- | --- |
| | Weekdays | Weekends | Mon | Tue | Wed | Thur | Fri | Sat | Sun |
| Average, mg/dL | 92 | 92 | 92 | 87 | 88 | 94 | 96 | 92 | 92 |
| Std. Dev, mg/dL | 15 | 12 | 11 | 17 | 15 | 14 | 15 | 10 | 13 |
| Number of Readings | 148 | 79 | 30 | 23 | 28 | 36 | 31 | 32 | 47 |
| Very Highs, >300 | | | | | | | | | |
| Highs, 156-300 | | | | | | | | | |
| In Target, 65-155 (as %) | 97 | 100 | 100 | 87 | 93 | 100 | 100 | 100 | 100 |
| Lows, 51-64 (as %) | 3 | | | 13 | 7 | | | | |
| Very Lows, <51 | | | | | | | | | |

The weight of the male subject with early stage Type 2 diabetes mellitus was also monitored during extended periods of administration on GNTI, decreasing from a baseline body mass index (BMI) of 25 to an average BMI of 22.8, corresponding to a reduction by about 9%.

EXAMPLE 2

Evaluation of Blood Glucose in Rhesus Monkeys

A cohort of rhesus monkeys having progressively increasing degrees of impaired glucose tolerance were monitored following an oral dose of GNTI of 86 ng/kg of body weight. Baseline readings of blood glucose (BG), high density lipoprotein C(HDL-C) and triglycerides (TG) were taken on Day 0. Table 5 shows the baseline readings on Day 0 and the results of the second reading on Day 8 of BG, HDL-C and TG.

TABLE 5

| Animal | Sequence | Oral Dose GNTI | BG mg/dL | HDL-C mg/dL | TG mg/dL |
| --- | --- | --- | --- | --- | --- |
| r89163 | Baseline | | 65 | 64 | 59 |
| | Day 0 | 86 ng/kg | | | |
| | Day 8 | | 63 | 84 | 60 |
| | Change | | (−3%) | (+)31% | (−−) |
| r98068 | Baseline | | 71 | 81 | <45 |
| | Day 0 | 86 ng/kg | | | |
| | Day 8 | | 51 | 85 | <45 |
| | Change | | (−)29% | (+)5% | (−−) |

TABLE 5-continued

| Animal | Sequence | Oral Dose GNTI | BG mg/dL | HDL-C mg/dL | TG mg/dL |
| --- | --- | --- | --- | --- | --- |
| r96027 | Baseline | | 74 | 44 | 112 |
| | Day 0 | 86 ng/kg | | | |
| | Day 8 | | 53 | 46 | 89 |
| | Change | | (−) 28% | (+) 10% | (−) 10% |
| r00072 | Baseline | | 80 | 48 | <45 |
| | Day 0 | 86 ng/kg | | | |
| | Day 8 | | 67 | 6.1 | <45 |
| | Change | | (−) 16% | (+) 27% | (−−) |
| r01078 | Baseline | | 81 | 51 | <45 |
| | Day 0 | 86 ng/kg | | | |
| | Day 8 | | 56 | 63 | <45 |
| | Change | | (−) 30% | (+) 24% | (−−) |

The effect of GNTI was most readily seen in the change of blood glucose and blood lipid levels. Subject r89163 had a baseline blood glucose level of 65, i.e., a "normal" fasting blood glucose level for a rhesus monkey. The other 4 subjects of the cohort, i.e., r98060, r96027, r00072, r01078, had baseline blood glucose levels ranging from 71-81 and were considered to have impaired glucose tolerance. On day 8, the subjects having impaired glucose tolerance showed a decrease in blood glucose ranging from 16%-30% with an average of 26%. Comparatively, the glucose "normal" subject (r89163), receiving the same GNTI dose, exhibited a decrease in blood glucose levels of 3% only, and in a glucose dependent manner, a characteristic feature of physiological incretin action. The lipid "normal subject (r98068) exhibited an increase in HDL-C lipid levels of only 5%, where the four dyslipidemic subjects (r89163, r96027, r00072, r01078) exhibited an HDL-C increase in the range of 10-31%, with an average of 23%.

EXAMPLE 3

Development of a Meal Tolerance Test (MTT)

To test for the effect of physiological first phase insulin secretion, a meal tolerance test (MTT) was developed. The meal tolerance test involved oral administration of meal based nutrients within suitable ratios of carbohydrates, proteins and fats. The ratios used for the given example were 70% carbohydrates, 8% protein and 22% fats. Prior to administration of a MTT to subject r89163, baseline blood glucose, insulin and glucagon readings were taken as seen in Table 6. Following MTT administration, the same readings were taken at time points of 3-9 minutes to test for first-phase insulin secretion and the subsequent reduction in blood glucose. It was determined that a first-phase insulin secretion dependent slight increase in insulin concentration appeared, typically, at 5 minutes post MTT administration, followed by a corresponding blood glucose decrease at 7 minutes. A slight decrease in glucagon levels was also coupled with first-phase insulin secretion at 5 minutes. The MTT serves as a corollary to the intravenous glucose tolerance test (IVGTT) and better measures first-phase insulin secretion because oral administration of nutrients has a more direct effect on the incretin effect.

TABLE 6

| Animal | Test Points Min | Drug | TestMealCal C/P/F (%) | BG Mg/dL | Insulin microU/mL | GIP Pg/mL | GLP-1 Pmol/L | Glucagon Pg/mL | Glucagon Change T0-T60/120 |
|---|---|---|---|---|---|---|---|---|---|
| R89163 | | None | 70/8/22 | | | | | | |
| | T-0 | | | 69.8 | 24.43 | | | 506.96 | |
| | | | | Test Meal Administration | | | | | |
| | T-3 | | | 73.3 | 15.17 | | | 506.86 | |
| | T-4 | | | 73.3 | 28.85 | | | 517.64 | |
| | TP5/Ins. | | | 76.7 | 34.63 | | | 480.54 | |
| | T-6 | | | 76.1 | 32.8 | | | 456.43 | |
| | TP7/BG | | | 74.3 | 32.02 | | | 430.75 | |
| | T-8 | | | 75.5 | 24.81 | | | 448.98 | |
| | T-9 | | | 75.6 | 24.73 | | | 481.24 | |

EXAMPLE 4

Application of the Meal Tolerance Test

Table 7 illustrates administration of the MTT to two rhesus monkeys categorized as metabolically "normal" based on "normal" fasting blood glucose values. The monkeys were given a diet of 55-60% carbohydrates, 15-25% protein, and 15-30% fat. Readings of blood glucose, insulin, and glucagon were taken at time points 0, 5, 7, 60 and 120 minutes. Additionally, at the same time points, the incretin hormones, GIP and GLP-1 were measured to more directly measure the incretin effect. In subject r98038, a significant increase in insulin and concurrent drop in glucagon were seen at time point 5, as would be expected. One hour after MTT administration very significant increases in insulin, GIP and GLP-1 were seen in subject r98038, again coupled with consecutive decreases in glucagon. Comparison of blood glucose levels at time points 0 and 120 minutes illustrates that normal metabolic functioning has returned the subject's blood glucose levels to normal within 120 minutes of MTT administration.

By contrast, subject r91081 appears from its baseline blood glucose level to be a "normal" metabolic subject. However, the characteristic first-phase insulin secretion at time point 5 following MTT administration is lacking as is the time point 7 blood glucose decrease. Further analysis showed that at 120 minutes following MTT administration the blood glucose and glucagon values were markedly higher than the baseline readings. These results contradict the results for "normal" subject r98038, and strongly indicate impaired metabolic control which was not discernable from the fasting blood glucose value.

TABLE 7

| Animal | Test Points Min | Drug | TestMealCal C/P/F (%) | BG Mg/dL | Insulin microU/mL | GIP Pg/mL | GLP-1 pmol/L | Glucagon Pg/mL | Glucagon Change T0-T60/120 |
|---|---|---|---|---|---|---|---|---|---|
| r98038 | | None | 74/6/20 | | | | | | |
| | TP 0 min | | | 58.15 | 15.68 | <8 | 12.8 | 180.79 | |
| | TP 5 min | | | 70 | 25.52 | <8 | 13.6 | 145.5 | |
| | TP 7 min | | | 71.15 | 17.16 | <8 | 11.3 | 243.26 | |
| | TP 60 min | | | 53.7 | 108.56 | 640 | 26.6 | 182.7 | (+) 1% |
| | TP 120 min | | | 56.3 | 43.97 | 560 | 34.9 | 138.22 | (−) 23% |
| r91081 | | None | 70/8/22 | | | | | | |
| | TP 0 min | | | 56.15 | 24.71 | 175 | 196 | 99.8 | |
| | TP 5 min | | | 63.05 | 32.44 | 160 | 178 | 95.4 | |
| | TP 7 min | | | 64.5 | 59.48 | 150 | 146 | 90.51 | |
| | TP 60 min | | | 63.85 | 111.1 | 950 | 141 | 114.49 | (+) 14.7% |
| | TP 120 min | | | 78.15 | 202.29 | 950 | 124 | 145.32 | (+) 45.6% |

EXAMPLE 5

Table 8 illustrates the effect of GNTI on physiologic control of glucagon levels. Baseline readings were taken on Day 1 of blood glucose, insulin, glucagon, GIP, and GLP-1 in metabolically impaired rhesus monkeys as determined through administration of the MTT. Cumulative in-situ doses of 45 ng/kg and 95 ng/kg were active on day 5 and day 7, respectively, during administration of the MTT. Readings of blood glucose, insulin, glucagon, GIP, and GLP-1 were taken at time points 0, 60 minutes and 120 minutes. As Table 8 illustrates, both dosages resulted in a marked decrease in glucagon at both time points 60 and 120 in all subjects tested. Comparison to untreated subject r91081 in Table 7 further demonstrates the marked decrease in glucagon.

TABLE 8

| Animal | Test Points 0/60/120 Minutes | GNTI ng/kg | TestMealCal C/P/F (%) | BG mg/dL | Insulin microU/mL | GIP pg/mL | GLP-1 pmol/L | Glucagon pg/mL | Glucagon Change T0-T60/120 |
|---|---|---|---|---|---|---|---|---|---|
| r96022 | | | | | | | | | |
| Day 1 | Baseline | No Drug | | 64 | 16 | 25 | 13 | 394 | |
| Day 5 | TP 0 min | 45 ng/kg | 73/9/18 | 51 | 14 | 8 | 11 | 411 | |
| | TP 60 min | | | 64 | 122 | 650 | 31 | 267 | −35% |
| | TP 120 min | | | 67 | 200 | n/a | 31 | 261 | −36% |
| Day 7 | TP 0 min | 95 ng/kg | 74/7/19 | 56 | 14 | 30 | 28 | 472 | |
| | TP 60 min | | | 70 | 100 | 675 | 35 | 240 | −49% |
| | TP 120 min | | | 63 | 54 | 675 | n/a | 271 | −43% |
| rh2251 | | | | | | | | | |
| Day 1 | Baseline | No Drug | | 76 | 11 | 140 | 13 | 377 | |
| Day 5 | TP 0 min | 45 ng/kg | 73/9/18 | 83 | 57 | 50 | 34 | 411 | |
| | TP 60 min | | | 98 | 396 | 640 | 83 | 366 | −11% |
| | TP 120 min | | | 78 | 249 | 760 | 82 | 249 | −39% |
| Day 7 | TP 0 min | 95 ng/kg | 75/6/19 | 82 | 71 | 25 | 60 | 487 | |
| | TP 60 min | | | 106 | 401 | 675 | n/a | 351 | −28% |
| | TP 120 min | | | 95 | 307 | 775 | 223 | 267 | −45% |
| rh2258 | | | | | | | | | |
| Day 1 | Baseline | No Drug | | 74 | 15 | n/a | 10 | 316 | |
| Day 5 | TP 0 min | 45 ng/kg | 74/8/18 | 69 | 23 | n/a | 19 | 302 | |
| | TP 60 min | | | 70 | 145 | 320 | 49 | 172 | −43% |
| | TP 120 min | | | 76 | 137 | 775 | 79 | 122 | −60% |
| Day 7 | TP 0 min | 95 ng/kg | 74/7/19 | 73 | 30 | 20 | 67 | 293 | |
| | TP 60 min | | | 69 | 54 | 75 | 60 | 107 | −63% |
| | TP 120 min | | | 86 | 71 | 240 | 77 | 108 | −63% |

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope.

What is claimed is:

1. A method of treating type 2 diabetes mellitus comprising administering to a subject a therapeutically effective amount of a selective κ-receptor antagonist, or a pharmaceutically acceptable derivative thereof, wherein a μ-agonist is not co-administered and wherein the selective κ-receptor antagonist is characterized by its μ/K antagonism $K_e$ selectivity ratio, the ratio being greater than 35, and further wherein the selective κ- receptor antagonist is administered daily in an amount from about 8 ng to about 80 ng per kg of body weight daily.

2. The method of claim 1, wherein the selective κ-receptor antagonist is guanidinylated naltrindole (GNTI).

3. The method of claim 1, wherein the selective κ-receptor antagonist is administered sublingually, orally, enterally, parenterally, topically, systemically or injected intravascularly, subcutaneously, peritoneally.

4. The method of claim 1, further comprising co-administration of an effective amount of an insulinogenic agent.

5. The method of claim 4, wherein the insulinogenic agent is an extended release composition.

* * * * *